United States Patent
Chen

(10) Patent No.: US 7,820,443 B2
(45) Date of Patent: Oct. 26, 2010

(54) FAST METHOD OF TRANSFORMING COMPETENT CELLS

(75) Inventor: Tzu-Chih Chen, Taipei (TW)

(73) Assignee: Yeastern Biotech Co., Ltd., Taipei (TW)

( * ) Notice: Subject to any disclaimer, the term of this patent is extended or adjusted under 35 U.S.C. 154(b) by 292 days.

(21) Appl. No.: 11/370,179

(22) Filed: Mar. 8, 2006

(65) Prior Publication Data

US 2007/0212783 A1    Sep. 13, 2007

(51) Int. Cl.
*C12N 15/63* (2006.01)
*C12N 15/70* (2006.01)

(52) U.S. Cl. .................. 435/488; 435/471; 435/476

(58) Field of Classification Search ........ None
See application file for complete search history.

(56) References Cited

U.S. PATENT DOCUMENTS 6,864,088 B2   3/2005   Chen et al.
6,875,748 B2 *  4/2005   Manthorpe et al. ............ 514/44

OTHER PUBLICATIONS

Huff et al., Optimization of routine transformation of *Escherichia coli* with plasmid DNA.Biotechniques. Nov. 1990 ;9(5):570-2, 574, 576-7.*

Chung CT,et al., One-step preparation of competent *Escherichia coli*: transformation and storage of bacterial cells in the same solutionProc Natl Acad Sci U S A. Apr. 1989;86(7):2172-5.*
Pope B,et al., High efficiency 5 min transformation of *Escherichia coli*.Nucleic Acids Res. Feb. 1, 1996 ;24(3):536-7.*
M. Mandel et al., "Calcium-dependent Bacteriophage DNA Infection," J. Mol. Biol. vol. 53, pp. 159-162 (1970).
William J. Dower et al., "High efficiency transformation of *E.coli* by high voltage electroporation," Nucleic Acids Res., vol. 16, No. 13, pp. 6127-6145 (1988).
Efim I. Golub, "One minute' transformation of competent *E.coli* by plasmid DNA," Nucleic Acids Res., vol. 16, No. 4, p. 1641 (1988).
Hiroaki Inoue et al., "High efficiency transformation of *Escherichia coli* with plasmids," Gene, vol. 96, pp. 23-28 (1990).
Douglas Hanahan, "Studies on Transformation of *Escherichia coli* with Plasmids," J. Med. Biol., vol. 166, pp. 557-580 (1983).
Douglas Hanahan, "Plasmid Transformation of *Escherichia coli* and other Bacteria," Methods in Enzymology, vol. 204, pp. 63-113 (1991).

* cited by examiner

*Primary Examiner*—Maria Leavitt
(74) *Attorney, Agent, or Firm*—WPAT, P.C.; Anthony King

(57) ABSTRACT

The invention relates to a fast method of transforming competent cells, comprising:
a. mixing a plasmid DNA with the competent cells suspending within ionic solution to form a mixture;
b. plating the mixture on a warm selective medium; and
c. culturing the mixture on the medium;
wherein the ionic solution comprises divalent cation selected from the group consisting of $Ca^{2+}$, $Mg^{2+}$, $Mn^{2+}$, $Zn^{2+}$, $Cu^{2+}$, $Cd^{2+}$, $Fe^{2+}$, $Sr^{2+}$ and $Co^{2+}$, and provided that the ionic solution does not include $Ca^{2+}$ alone.

4 Claims, No Drawings

FAST METHOD OF TRANSFORMING COMPETENT CELLS

FIELD OF THE INVENTION

The present invention relates to a gene transformation method. In particular, the present invention relates to a fast method of transforming competent cells.

BACKGROUND OF THE INVENTION

E. coli is the most widely applied microorganism. Especially in the field of molecular biology and genetic engineering, E. coli variants are essential host cells used in labs for mass-producing different kinds of DNAs or proteins. The technology of delivering DNA molecules in the surrounding medium into host cells is called transformation, and the host cells after preliminary treatment to be more permeable to DNA molecules are called competent cells.

Hence, producing competent cells and transforming competent cells is very important in view of recent developments of genetic engineering. The technology described above can be retraced to Mandel, M. and Higa, A. (J. Mol. Biol. 53:159-162), who published a chemical transformation method using $CaCl_2$. After 30-year-improvement, the time needed for transformation is still 1.5-3.0 hours because the host cells are injured by the chemical treatment. The injured host cells require a recovery step. In the recovery step, the host cells are cultured in a nutrient medium to allow the injured host cells to recover their physiological function and drug resistance. Then the host cells are plated on a selective medium to screen for transformed host cells. Otherwise, the transformation efficiency would decrease by several times. Recently, a fast transformation method called electroporation can deliver DNA molecules into the E. coli host cells by transient current. However, the host cells after the transient current treatment still need one hour of recovery to obtain a higher transformation efficiency (Dower et. al., 1988 Nucleic Acids Res. 16: 6127-6145). In 1988, Golub E. I. (Nucleic Acids Res. 16: 1641) published a method of one-minute transformation. Although a recovery step is performed, the transformation efficiency is only $10^4$-$10^5$ colonies/µg plasmid DNA.

A fast method of transformation (U.S. Pat. No. 6,864,088), in which the long and time-consuming recovery step of competent cells is omitted from the conventional transformation method without reducing its transformation efficiency, has been developed by Yeastern Biotech Co., Ltd in recent years. The fast method comprises the following steps: mixing plasmid DNA and the competent cells in a tube, heat-shock treatment of the mixture, and then plating the mixture on a selective medium of lower temperature with a plating tool of lower temperature. The recovery step of adding non-selective medium (e.g., SOC, LB . . . ) is omitted. Therefore the conventional multi-step transforming procedure taking 1.5~3.0 hours is shortened to a few minutes and can be completed within one single tube, without reducing its transformation efficiency.

Although said method of transforming competent cells is better than prior arts, a temperature-control apparatus for heat-shock treatment is still indispensable. Further, the cells may not be heated evenly when placed in a tube. Hence, it will save a large amount of time, expenses and efforts if an innovative method of transformation is developed in which the time-consuming recovery step of the transformed cells is omitted, a temperature-control apparatus is not required, cells may not be heated unevenly and the transformation efficiency may not be reduced.

DETAILED DESCRIPTION OF THE INVENTION

The present invention provides a fast method of transforming competent cells. The method is characterizes in simplifying the procedure for heat-shock treatment, preventing from the phenomenon that the cells are heated unevenly, omitting the long and time-consuming recovery step of transformed Escherichia coli (E. coli) cells and not reducing the original transformation efficiency.

The competent cells can be prepared from various microorganisms, most preferably from various E. coli strains such as HB101, DH5-alpha., GM2929, XL1-Blue, TG1, BL21, and JM109, etc. E. coli is the most widely applied microorganism. Especially in the field of molecular biology and genetic engineering, E. coli variants are obligate host cells used in labs for mass-producing different kinds of DNAs or proteins. The host cells after preliminary treatment to be more permeable to DNA molecules are called competent cells, and the technology of delivering DNA molecules in the surrounding medium into host cells is called transformation.

According to the fast method of transforming E. coli disclosed in U.S. Pat. No. 6,864,088, plasmid DNA and competent cells were mixed, the mixture was subjected to heat-shock treatment, and then plated on a cool selective medium with a cool plating tool for culturing transformants selectively.

In addition to possessing the advantages of the above-mentioned method (especially omitting the time-consuming recovery step of the transformed cells), the present invention further simplifies the step of heat-shock treatment by spreading the mixture of plasmid DNA and competent cells directly on a selective medium of a higher temperature. The cells are subjected to heat-shock treatment directly through the temperature of the selective medium.

The present invention provides a fast method of transforming competent cells, comprising:

a. mixing a plasmid DNA with the competent cells suspending within ionic solution to form a mixture;
b. plating the mixture on a warm selective medium; and
c. culturing the mixture on the medium.

Said ionic solution within which the competent cells suspend comprises divalent cation selected from the group consisting of $Ca^{2+}$, $Mg^{2+}$, $Mn^{2+}$, $Zn^{2+}$, $Cu^{2+}$, $Cd^{2+}$, $Fe^{2+}$, $Sr^{2+}$ and $Co^{2+}$, and the ionic solution does not include $Ca^{2+}$ alone. In the most preferred embodiment, the divalent cation is $Mg^{2+}$. Concentration of the divalent cation is 5 mM to 500 mM, more preferably 10 mM to 300 mM, most preferably 30 mM to 150 mM. The ionic solution can further comprise monovalent cation selected from the group consisting of $NH_4^+$, $Li^+$, $Na^+$, $K^+$, $Rb^+$, $Cs^+$, $Ag^+$ and $Co^+$. In the most preferred embodiment, the monovalent cation is $Rb^+$. Concentration of the monovalent cation is 10 mM to 1000 mM, more preferably 20 mM to 600 mM, most preferably 60 mM to 300 mM. The ionic solution can further comprise trivalent cation selected from the group consisting of $Al^{3+}$, $Cr^{3+}$, $Fe^{3+}$ and $Co^{3+}$. In the most preferred embodiment, the trivalent cation is $Co^{3+}$.

Generally the transformation efficiency exceeds $10^6$, more preferably exceeds $10^7$, and most preferably exceeds $10^8$.

The recovery step of adding culture medium is dispensable in the invention. That is, adding non-selective medium for incubation for tens of minutes before plating on a warm selective medium is not necessary. Heat-shock treatment is also dispensable in the invention. That is, heat-shock treatment before plating on a warm selective medium is not necessary. The temperature of the warm selective medium ranges from 20° C. to 50° C., preferably from 25° C., to 45° C., more preferably from 30° C. to 42° C.

The substitution of plating on warm selective medium for conventional heat-shock treatment by pre-warmed temperature-control apparatus has three advantages: (1) FASTER—saving the time of conventional heat-shock treatment; (2) EASIER—no need for preparation of the pre-warmed temperature-control apparatus and easier for laboratory work; (3) CELLS EVENLY HEATED—the cells are not heated indirectly via the wall of the tubes but evenly heated via spreading on warm selective medium. Because a wider interface between the cells and the heat source exists that way, the cells are evenly heated.

The fast method of the invention can further comprise one or more steps between mixing plasmid DNA with the competent cells suspending within ionic solution to form a mixture and plating the mixture on a warm selective medium selected from the group consisting of: incubating the mixture of plasmid DNA and competent cell in an ice bath; and heating the mixture of plasmid DNA and competent cell to perform heat-shock. The temperature of the heat-shock ranges from 20° C. to 50° C., more preferably from 34° C. to 45° C.

Between the steps of plating the mixture on a warm selective medium and culturing the mixture on the medium, the fast method of the invention can further selectively comprise a cool-down treatment, namely cooling the warm selective medium in a cool environment. The cool environment is at room temperature, in an ice bath, a cooling apparatus, a freezing apparatus or under any circumstances where the temperature is lower than the warm selective medium. The temperature of the cool environment ranges from −35° C. to 30° C., more preferably from −20° C. to 20° C., most preferably from −10° C. to 10° C.

The plasmid DNA mixed with the competent cells in the invention is a general plasmid DNA or a recombinant plasmid DNA, preferably the recombinant plasmid DNA.

The selective medium in the invention are medium added with antibiotics. In a preferred embodiment, the selective medium is added with an antibiotic selected from the group consisting of ampicillin, kanamycin, chloramphenicol, tetracycline, erythromycin, methotrexate, hygromycin, neomycin and zeocine.

*E. coli* is Gram negative and the preparation of the most competent cells of Gram negative or Gram positive bacteria is modified from the transformation method of *E. coli* (Method In Enzymology 204: 63-113, Method in Microbiology 21: 79-128). Therefore, the fast transformation method may be applied to the transformation of competent cells of Gram negative or Gram positive bacteria. In a preferred embodiment, the competent cells in the invention are prepared from *E. coli*.

The examples below are non-limiting and are merely representative of various aspects and features of the present invention.

EXAMPLE

Example 1

Materials

ECOS competent cells from Yeastern Biotech Co., Ltd were prepared according to the method of Inoue H., 1990, Gene 96:23-28 combined with that of Hanahan D., 1983, J. Mol. Bio. 166:557-580. The ECOS cells were tested in the following examples, and the competent cells prepared from conventional CaCl$_2$ method (Mandel, M., and Higa A. 1970, J. Mol. Biol. 53: 159-162) were used as control. ECOS-101 competent cells were suspended in a solution containing 50 mM Mg$^{2+}$ and 100 mM Rb$^+$, while the conventional competent cells were suspended in a solution containing 100 mM CaCl$_2$.

Example 2

Warm Selective Medium Substituted for Conventional Heat-Shock Treatment

The above-mentioned cells (strain DH5-alpha) were transformed with plasmid pBR322. Aliquots of competent cells (100 μl/aliquot) were taken out from 30° C. freezer and thawed in water bath at room temperature or with tap water until ⅓ thawed (10~20 sec.). Plasmid pBR322 were added immediately and the tube was vortexed for 0.5~1 sec. Concentrations of the plasmid pBR322, both for adding to ECOS cells and for adding to the conventional competent cells prepared with CaCl$_2$ method, were 10$^5$ μg/ml. Some of the samples were immediately subjected to heat-shock treatment with 42° C. water bath for 2 minutes, and the others were not. The tubes were flipped for well mixing the mixture. Half of the samples were added with 900 μl of non-selective medium (LB) and incubated at 37° C. for 40 minutes before plated on antibiotics-added selective medium, while others were directly plated on antibiotics-added selective medium. The selective medium used was 4° C. or 37° C. Temperature of the plating tools were the same as that of its corresponding selective medium. The resulted transformation efficiency was as follows:

TABLE 1

Effects of heat-shock treatment and selective medium at different temperature on transformation efficiency

| | | Temperature of culture medium | ECOS | CaCl$_2$ |
|---|---|---|---|---|
| Heat-shock treatment for 2 minutes | Recovery by adding LB | 4° C. | $6.44 \times 10^7$ | $7.14 \times 10^5$ |
| | | 37° C. | $5.65 \times 10^6$ | $6.96 \times 10^5$ |
| | Plating directly | 4° C. | $4.32 \times 10^7$ | $4.12 \times 10^5$ |
| | | 37° C. | $7.15 \times 10^6$ | $3.32 \times 10^5$ |
| No heat-shock treatment | Recovery by adding LB | 4° C. | $2.36 \times 10^7$ | $4.48 \times 10^5$ |
| | | 37° C. | $3.72 \times 10^7$ | $9.75 \times 10^4$ |
| | Plating directly | 4° C. | $1.02 \times 10^7$ | $1.38 \times 10^6$ |
| | | 37° C. | $9.58 \times 10^7$ | $1.17 \times 10^6$ |

It is concluded from the foregoing table that:

(1) The recovery step of adding LB is dispensable: Omitting the recovery step of adding LB and plating the mixture directly made no obvious differences on transformation efficiency. Transformation efficiency of ECOS competent cell was still maintained on the level of $5 \times 10^6 \sim 10^8$.

(2) The step of heat-shock treatment is also dispensable: Omitting the 42° C. water bath heat-shock treatment made no difference on transformation efficiency. Transformation efficiency of ECOS competent cell was still maintained on the level of $10^7 \sim 10^8$, while that of conventional competent cell was only $10^5 \sim 10^6$.

(3) Warm selective medium enhances transformation efficiency of the specially formulated ECOS competent cell: Under the condition that the recovery step of adding LB and heat-shock treatment were simultaneously omitted, and that the 37° C. selective medium was used in substitution for 4° C. selective medium, the resulted transformation efficiency was enhanced to 9-folds. However, transformation efficiency of conventional CaCl$_2$ method was not improved.

Example 3

The Wide Applicability to Various Strains and Various Selective Medium Temperature of the Fast Transformation Method The ECOS competent cells of *E coli* strains DH5-alpha, JM109, BL21 (DE3) and XL1 Blue were used and suspended in water solution containing 50 mM Mg$^{2+}$ and 100 mM Rb$^+$. Methods of example 2 were used to test warm selective medium of various temperature. The results were as follows:

TABLE 2

Transformation efficiency of different strains plated on selective medium at different temperature

| Strain | Heatshock 4° C. | Non-Heatshock | | | |
|---|---|---|---|---|---|
| | | 4° C. | 25° C. | 37° C. | 42° C. |
| DH5-alpha | 4.3 × 10$^7$ | 1.0 × 10$^7$ | — | 9.6 × 10$^7$ | — |
| JM109 | 6.4 × 10$^7$ | 4.0 × 10$^7$ | — | 7.1 × 10$^7$ | — |
| BL21(DE3) | 1.3 × 10$^7$ | 1.5 × 10$^6$ | 8.8 × 10$^6$ | 1.2 × 10$^7$ | 1.5 × 10$^7$ |
| XL1Blue | 4.8 × 10$^7$ | 1.2 × 10$^7$ | 8.2 × 10$^7$ | 1.1 × 10$^8$ | 4.5 × 10$^7$ |

Given the above table, it is demonstrated that:

(1) The fast transformation method has a wide applicability to various *E. coil* strains: The transformation efficiency of strain DH5-alpha, JM109, BL21 (DE3) and XL1 Blue all exceeds 8×10$^6$.

(2) The fast transformation method has a wide applicability to selective medium at different temperature: Plating on 25° C., 37° C. and 42° C. selective medium resulted in similar effects.

Example 4

The Wide Applicability to Selective Medium of Various Antibiotics of the Fast Transformation Method Various kinds of antibiotics were added in warm selective medium and tested with a 7.4 kb plasmid (pBP325 derivatives containing antibiotic marker Ap$^r$, Tc$^r$ and Cm$^r$). The results were as follows:

TABLE 3

Effects of different antibiotics on transformation efficiency

| | pBR325-KR(7.4 kb) 10$^{-5}$ µg |
|---|---|
| Ampicilin (30 µg/ml) | 2.6 × 10$^7$ |
| Ampicilin (50 µg/ml) | 2.2 × 10$^7$ |
| Tetracyclin (7.5 µg/ml) | 1.3 × 10$^7$ |
| Chloramphenicol (20 µg/ml) | 1.4 × 10$^7$ |
| Chloramphenicol (25 µg/ml) | 1.2 × 10$^7$ |

It is obvious that the resulted transformation efficiency were about the same, demonstrating the wide applicability to selective medium of various antibiotics of the present invention.

Example 5

The Wide Applicability to Plasmids of Various Sizes of the Fast Transformation Method ECOS competent cells were tested with plasmids of different size. The results were as follows:

TABLE 4

Transformation efficiency of plasmid DNA with different sizes

| | pUC19 (2.7 kb) | pBR325-KR(7.4 kb) | pMS12 (10 kb) |
|---|---|---|---|
| Sigma Amp (30 µg/ml) | 3.2 × 10$^8$ | 2.6 × 10$^7$ | 2.2 × 10$^6$ |
| Sigma Amp (50 µg/ml) | 3.4 × 10$^8$ | 2.2 × 10$^7$ | 2.1 × 10$^6$ |

It is concluded from the above table that the transformation efficiency of ECOS competent cell with plasmids of different sizes exceeds 10$^6$. It is demonstrated that the method is widely applicable to plasmid of various sizes and different concentration of antibiotics.

What is claimed is:

1. A fast method of transforming competent cells prepared from *Escherichia coli* with a high transformation efficiency consisting of:
    (a) mixing a plasmid DNA with the competent cells suspending within ionic solution to form a mixture;
    (b) plating the mixture on a warm selective medium at temperature of 25° C.-45° C. without heat-shock treatment and recovery step which requires adding broth medium; and
    (c) culturing the mixture on the medium; wherein the high transformation efficiency is over 10$^7$ transformants/µg DNA, wherein the ionic solution comprises a monovalent cation selected from the group consisting of NH$^{4+}$, Li$^+$, Na$^+$, K$^+$, Rb$^+$, Cs$^+$, Ag$^+$ and Co$^+$ and a divalent cation selected from the group consisting of Ca$^{2+}$, Mg$^{2+}$, Mn$^{2+}$, Zn$^{2+}$, Cu$^{2+}$, Cd$^{2+}$, Fe$^{2+}$, Sr$^{2+}$ and Co$^{2+}$, provided that the ionic solution does not include Ca$^{2+}$ alone, and wherein the selective medium is added with an antibiotic selected from the group consisting of ampicillin, kanamycin, chloramphenicol, tetracycline, erythromycin, methotrexate, hygromycin, neomycin and zeocine.

2. The fast method of claim 1, wherein the divalent cation is in concentration of 5 mM~500 mM.

3. The fast method of claim 1, wherein the monovalent cation is in concentration of 10 mM~1000 mM.

4. The fast method of claim 1, wherein the warm selective medium is at temperature of 30° C.~42° C.

\* \* \* \* \*